United States Patent [19]

Mizutare et al.

[11] Patent Number: 5,808,092

[45] Date of Patent: Sep. 15, 1998

[54] PROCESS FOR PREPARING-1-ETHYL-5-HYDROXYPYRAZOLE

[75] Inventors: Katsuhiko Mizutare; Takafumi Hirakawa; Ken Ikuno, all of Ube, Japan

[73] Assignee: UBE Industries, Ltd., Ube, Japan

[21] Appl. No.: 950,991

[22] Filed: Oct. 15, 1997

[30] Foreign Application Priority Data

Oct. 18, 1996 [JP] Japan .................................. 8-275933

[51] Int. Cl.$^6$ ............................................... C07D 231/20
[52] U.S. Cl. ....................................................... 548/366.1
[58] Field of Search ........................................ 548/366.1

[56] References Cited

FOREIGN PATENT DOCUMENTS 61-189271  8/1986  Japan .

*Primary Examiner*—Robert W. Ramsuer
*Attorney, Agent, or Firm*—David G. Conlin

[57] ABSTRACT

Disclosed is a process for preparing 1-ethyl-5-hydroxypyrazole, which comprises reacting an alkyl 3-alkoxyacrylate represented by the following formula (1):

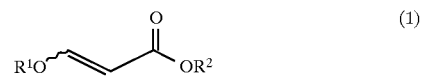

wherein $R^1$ and $R^2$ are the same or different from each other and each represent a lower alkyl group, and ⚡ in the formula represents either cis- or trans-configuration, with ethylhydrazine in an amount of 1- to 10-fold mole based on 1 mole of the alkyl 3-alkoxyacrylate in a weakly basic aqueous solvent.

10 Claims, No Drawings

PROCESS FOR PREPARING-1-ETHYL-5-HYDROXYPYRAZOLE

BACKGROUND OF THE INVENTION

This invention relates to a novel process for preparing 1-ethyl-5-hydroxypyrazole (described in, for example, Japanese Provisional Patent Publication No. 44375/1991) which is a known useful compound as an intermediate of an effective compound of agricultural chemicals, particularly a herbicide.

As a preparation process which is the closest to the process for preparing 1-alkyl-5-hydroxypyrazole of the present invention, a preparation process described in Japanese Provisional Patent Publication No. 189271/1986 may be mentioned. In Japanese Provisional Patent Publication No. 189271/1986, there has been disclosed a process for synthesizing 1-methyl-5-hydroxypyrazole by reacting an alkyl 3-alkoxyacrylate represented by the following formula:

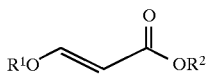

wherein $R^1$ and $R^2$ are the same or different from each other and each represent a lower alkyl group, with methylhydrazine in an amount of 0.5- to 5-fold mole (preferably 0.8- to 2-fold mole) based on 1 mole of the alkyl 3-alkoxyacrylate in the absence of a solvent or in an organic solvent at 0° to 100° C. for 1 to 24 hours.

When 1-methyl-5-hydroxypyrazole is synthesized by the disclosed process, a high yield of 90% or more is obtained. However, as shown in Comparative example 5 described below, when 1-ethyl-5-hydroxypyrazole is synthesized by the disclosed process, its yield is as low as 70% or less, and there is a problem that a large amount of impurities such as an isomer and a 4,4'-adduct as shown in Table 1 are generated.

TABLE 1

| Isomer | 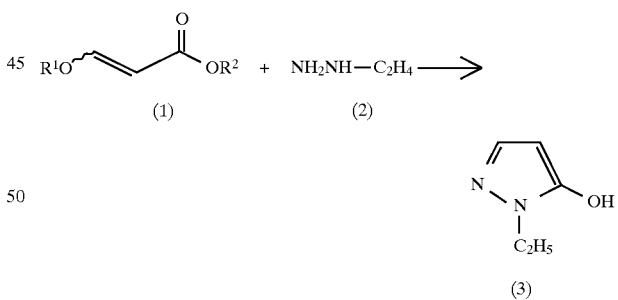 |
|---|---|
| 4,4'-Adduct | |

SUMMARY OF THE INVENTION

An object of the present invention is to provide a novel process for preparing 1-ethyl-5-hydroxypyrazole which is useful as an intermediate of an effective compound of agricultural chemicals, particularly a herbicide, with a good yield while generation of impurities is suppressed.

The present inventors have studied in order to solve the above problems and consequently found a novel process for preparing 1-ethyl-5-hydroxypyrazole, to accomplish the present invention.

That is, the first invention relates to a process for preparing 1-ethyl-5-hydroxypyrazole, which comprises reacting an alkyl 3-alkoxyacrylate represented by the following formula (1):

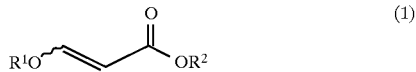

wherein $R^1$ and $R^2$ are the same or different from each other and each represent a lower alkyl group, and ∽ in the formula represents either cis- or trans-configuration, with ethylhydrazine in an amount of 1- to 10-fold mole based on 1 mole of the alkyl 3-alkoxyacrylate in a weakly basic aqueous solvent.

The second invention relates to a process for isolating 1-ethyl-5-hydroxypyrazole, which comprises concentrating the reaction mixture obtained in the first invention under reduced pressure to remove ethylhydrazine and then crystallizing the residue by salting out.

DESCRIPTION OF THE PREFERRED EMBODIMENTS

In the following, the present invention is explained in detail.

In the present invention, as shown below, the desired 1-ethyl-5-hydroxypyrazole (compound (3)) can be prepared by reacting an alkyl 3-alkoxyacrylate (compound (1)) with ethylhydrazine (compound (2)) in a weakly basic aqueous solvent, with a good yield while generation of impurities is suppressed.

In the compound of the formula (1), $R^1$ and $R^2$ each represent a lower alkyl group, preferably having 1 to 6 carbon atoms, more preferably having 1 to 4 carbon atoms, further preferably a methyl group and an ethyl group, particularly preferably a methyl group. $R^1$ and $R^2$ may be the same or different from each other.

In this invention, a weakly basic aqueous solvent means a solvent having pH of about 7.5 to about 10.0, preferably about 9.0 to about 10.0, more preferably about 9.2 to about 9.8, particularly preferably about 9.4 to about 9.6.

$$R^1O\overset{}{\diagup}\hspace{-1em}\diagdown\overset{O}{\underset{}{\diagdown}}OR^2 + NH_2NH-C_2H_4 \longrightarrow$$

(1)        (2)

[pyrazole structure with C₂H₅ and OH]

(3)

The desired 1-ethyl-5-hydroxypyrazole can be isolated by concentrating the obtained reaction mixture under reduced pressure to remove ethylhydrazine and then crystallizing the residue by salting out.

The compound (1) can be synthesized by, for example, synthesizing an alkyl 3,3-dialkoxypropionate according to the process described in Japanese Patent Publication No. 45974/1986 or Japanese Patent Publication No. 45975/1986, followed by heating in the presence of an acid.

As the compound (2), a commercially available product (for example, ethylhydrazine produced by Nippon Hydrazine Co., Japan) can be used.

In the present invention, an aqueous solvent is used.

As the aqueous solvent, there may be mentioned an aqueous solvent which comprises water as a main component and contains a small amount of an organic solvent, and water. From the points of a reaction rate and economy, water alone is preferably used.

The amount of the aqueous solvent to be used is preferably 1- to 50-fold volume based on the volume of the compound (1).

In order to suppress generation of impurities, it is particularly important to effect this reaction under a weakly basic condition, i.e., by maintaining pH of the reaction mixture during the reaction at about 7.5 to about 10.0, preferably at pH about 9.0 to about 10.0, more preferably at pH about 9.2 to about 9.8, particularly preferably at pH about 9.4 to about 9.6.

For adjusting the pH of the reaction mixture, it is preferably carried out to adjust pH of an ethylhydrazine aqueous solution within the range of about 7.5 to about 10.0 before initiating the reaction, more preferably about 9.0 to about 10.0, particularly preferably about 9.2 to about 9.8, most preferably about 9.4 to about 9.6. Since pH of the reaction mixture is decreased by adding dropwise alkyl 3-alkoxyacrylate to an ethylhydrazine aqueous solution, the pH of the ethylhydrazine aqueous solution is preferably set within the above range.

During the reaction, alkyl 3-alkoxyacrylate is added dropwise to an aqueous solution of ethylhydrazine. If ethylhydrazine is added to alkyl 3-alkoxyacrylate, 4,4'-adduct which is a by-product will be produced remarkably.

A reagent for adjusting the reaction condition to weakly basic is not particularly limited so long as the object of the present invention can be achieved. As the reagent, there may be mentioned an alkali metal compound such as lithium hydroxide, sodium hydroxide and potassium hydroxide, and an alkaline earth metal compound such as magnesium hydroxide and calcium hydroxide, preferably sodium hydroxide or potassium hydroxide.

The amounts of the starting compounds to be used are 1.0- to 10-fold mole, preferably 1.0- to 6-fold mole, more preferably 1.5- to 5-fold mole of the compound (2) based on 1 mole of the compound (1).

The reaction temperature is $-10°$ to $80°$ C., preferably $0°$ to $50°$ C.

The reaction time may vary depending on the amounts and concentrations of the starting compounds to be used and the reaction temperature, but it is generally 0.5 hour to 24 hours.

Generation of impurities may vary depending on the amounts and concentrations of the starting compounds to be used, pH of the reaction system and the reaction temperature. At pH 9.0 to 10.0, the isomer can be suppressed to 16% or less in terms of a peak area % measured by high performance liquid chromatography (HPLC), and the 4,4'-adduct can be suppressed to 10% or less with the same measure as the above. At pH 9.2 to 9.8, the isomer can be suppressed to 9% or less, and the 4,4'-adduct can be suppressed to 9% or less. Here, the terms "peak area %" mean a value (%) obtained by dividing a peak area of a certain impurity by a peak area of 1-ethyl-5-hydroxypyrazole measured by HPLC.

The yield of the desired compound (3) may vary depending on the amounts and concentrations of the starting compounds to be used, pH of the reaction system and the reaction temperature. The yield is 80% or more under the reaction conditions of the present invention, and 90% or more under the preferred conditions.

After completion of the reaction, 1-ethyl-5-hydroxypyrazole which is a desired compound obtained as described above can be isolated by concentrating the reaction mixture under reduced pressure to remove ethylhydrazine and then crystallizing the residue by salting out.

The concentration is carried out under a condition of atmospheric pressure to reduced pressure, preferably under a reduced pressure of 400 Torr or less so that the temperature of a concentrated solution becomes $80°$ C. or less.

Ethylhydrazine removed by this concentration operation can be used again by removing a lower alkyl component produced by the reaction, by distillation operation or the like.

Crystallization by salting out is carried out by neutralizing the concentrated solution with an acid.

As the acid to be used, there may be mentioned an inorganic acid such as hydrochloric acid, hydrobromic acid, sulfuric acid and phosphoric acid, and an organic acid such as formic acid, acetic acid and propionic acid, preferably formic acid, hydrochloric acid or hydrobromic acid.

This is because a produced salt has high solubility in water at a temperature range of $-10°$ to $50°$ C.

The neutralization is carried out at a temperature range of $-10°$ to $80°$ C., preferably a range of $0°$ to $50°$ C. By salting out, the desired compound, 1-ethyl-5-hydroxypyrazole is crystallized together with a salt produced by neutralization.

The amount of the acid to be added is preferably an amount equimolar with the amount of "ethylhydrazine used in the reaction—ethylhydrazine removed by concentration". The amount of the salt produced by neutralization is preferably 0.2 to 1.0 part by weight, preferably 0.3 to 0.5 part by weight based on the amount of the desired compound.

When the amount of the salt produced by neutralization is insufficient, the neutralization is carried out by separately adding the salt produced by neutralization until the amount reaches a suitable range.

The desired compound crystallized can be obtained by separating it by general filtration operation and, if necessary, drying it under reduced pressure.

EXAMPLES

The present invention is explained in detail by referring to Examples and Comparative examples. However, the range of the present invention is not limited by these Examples.

Example 1 (Synthesis of the Compound (3))

While stirring, 901.5 g (3.00 mole) of a 20% ethylhydrazine aqueous solution was cooled to $10°$ C. under ice cooling, and concentrated hydrochloric acid was slowly added dropwise to the solution to adjust pH to 9.8.

Further, 116.1 g (1.00 mole) of methyl 3-methoxypropionate was added dropwise to the mixture over about 1 hour, and the resulting mixture was reacted for 4 hours.

During the dropwise addition and after the dropwise addition, the reaction temperature was maintained at $10°$ C. By adding a 48% sodium hydroxide aqueous solution dropwise to the mixture at a suitable time, the pH of the mixture was maintained in the range of 9.4 to 9.6.

After completion of the reaction, the reaction mixture was analyzed by high performance liquid chromatography (HPLC) to find that methyl 3-methoxypropionate disappeared and 105.4 g (0.94 mole) of 1-ethyl-5-hydroxypyrazole which was the desired compound was produced (yield: 94.0%).

An isomer and a 4,4'-adduct which were impurities were analyzed by HPLC to find that they were produced in amounts of 1.6 area % and 1.1 area % based on the amount of the desired compound, respectively.

Also, unreacted ethyhydrazine was analyzed by gas chromatography (GC) to find that its amount was 115.6 g (1.92 mole).

Conditions of HPLC measurements (a) Analyses of the isomer and the desired compound
  Column: Inertsil ODS2 5 $\mu$ (trade name, produced by GL Science, Japan), 4.6 mm×250 mm
  Mobile phase: 900 ml of water+100 ml of methanol+ 11.02 g of phosphoric acid+1.02 g of potassium dihydrogen phosphate
  Column temperature: 45° C.
  Detection wavelength: UV 240 nm
  Retention time: 4.0 minutes for the desired compound, 5.7 minutes for the isomer (b) Analysis of the 4,4'-adduct
  Column: Inertsil ODS 10 $\mu$ (trade name, produced by GL Science, Japan), 4.6 mm×250 mm
  Mobile phase: 900 ml of water+100 ml of methanol+ 11.02 g of phosphoric acid+1.02 g of potassium dihydrogen phosphate
  Column temperature: 45° C.
  Detection wavelength: UV 240 nm
  Retention time: 3.9 minutes for the desired compound, 9.9 minutes for the 4,4'-adduct Conditions of GC measurement (analysis of ethylhydrazine)
  Column: PEG 6000, 25% Shimalite (BT) 60/80, 3 m
  Carrier gas: nitrogen
  Column temperature: temperature was elevated from 90° C. to 160° C. at 3° C./min
  Detector: FID Example 2 (Synthesis of the Compound (3))

While stirring 58.35 g (200 mmole) of a 20.6% ethylhydrazine aqueous solution, concentrated hydrochloric acid was slowly added dropwise to the solution at 20° C. to adjust pH to 9.8.

Further, 11.61 g (100 mmole) of methyl 3-methoxypropionate was added dropwise to the mixture over about 1 hour, and the resulting mixture was reacted for 6 hours.

During the dropwise addition and after the dropwise addition, the reaction temperature was maintained at 20° C. By adding a 48% sodium hydroxide aqueous solution dropwise to the mixture at a suitable time, the pH of the mixture was maintained in the range of 9.4 to 9.6.

After completion of the reaction, the reaction mixture was analyzed by high performance liquid chromatography (HPLC) to find that methyl 3-methoxypropionate disappeared and 10.36 g (92 mmole) of 1-ethyl-5-hydroxypyrazole which was the desired compound was produced (yield: 92.4%).

An isomer and a 4,4'-adduct which were impurities were analyzed by HPLC to find that they were produced in amounts of 1.6 area % and 3.3 area % based on the amount of the desired compound, respectively.

Example 3 (Synthesis of the Compound (3))

While stirring 62.56 g (200 mmole) of a 19.2% ethylhydrazine aqueous solution, concentrated hydrochloric acid was slowly added dropwise to the solution at 40° C. to adjust pH to 9.8.

Further, 15.48 g (133 mmole) of methyl 3-methoxypropionate was added dropwise to the mixture over about 1 hour, and the resulting mixture was reacted for 2 hours.

During the dropwise addition and after the dropwise addition, the reaction temperature was maintained at 40° C. By adding a 48% sodium hydroxide aqueous solution dropwise to the mixture at a suitable time, the pH of the mixture was maintained in the range of 9.4 to 9.6.

After completion of the reaction, the reaction mixture was analyzed by high performance liquid chromatography (HPLC) to find that methyl 3-methoxypropionate disappeared and 13.69 g (122 mmole) of 1-ethyl-5-hydroxypyrazole which was the desired compound was produced (yield: 91.6%).

An isomer and a 4,4'-adduct which were impurities were analyzed by HPLC to find that they were produced in amounts of 5.2 area % and 6.8 area % based on the amount of the desired compound, respectively.

Example 4 (Synthesis of the Compound (3))

While stirring 50.05 g (160 mmole) of a 19.2% ethylhydrazine aqueous solution, concentrated hydrochloric acid was slowly added dropwise to the solution at 40° C. to adjust pH to 9.8.

Further, 15.48 g (133 mmole) of methyl 3-methoxypropionate was added dropwise to the mixture over about 1 hour, and the resulting mixture was reacted for 3 hours.

During the dropwise addition and after the dropwise addition, the reaction temperature was maintained at 40° C. By adding a 48% sodium hydroxide aqueous solution dropwise to the mixture at a suitable time, the pH of the mixture was maintained in the range of 9.4 to 9.6.

After completion of the reaction, the reaction mixture was analyzed by high performance liquid chromatography (HPLC) to find that methyl 3-methoxypropionate disappeared and 12.32 g (110 mmole) of 1-ethyl-5-hydroxypyrazole which was the desired compound was produced (yield: 82.4%).

An isomer and a 4,4'-adduct which were impurities were analyzed by HPLC to find that they were produced in amounts of 9.0 area % and 9.1 area % based on the amount of the desired compound, respectively.

Example 5 (Removal of Unreacted Ethylhydrazine)

While heating by hot water at 70° C. and stirring, 1,096.8 g of the reaction mixture (containing 105.4 g of the desired compound and 115.6 g of ethylhydrazine) obtained in Example 1 was concentrated under reduced pressure at a vacuum degree of 100 to 6 mmHg until there was no fraction to be distilled out.

The distillate was analyzed by GC to find that 94.7 g of ethylhydrazine was contained.

Example 6 (Isolation of the Compound (3))

To the concentrated solution obtained in Example 4 was added 124.0 g of water, and concentrated hydrochloric acid was slowly added dropwise to the solution until the pH of the solution became 5.8.

During the dropwise addition of concentrated hydrochloric acid, the reaction mixture was cooled by a water bath so that the temperature thereof became 20° to 30° C. After the dropwise addition of concentrated hydrochloric acid, the reaction mixture was cooled by an ice bath so that the temperature thereof became 5° to 10° C., and stirred for 30 minutes.

The precipitated crystals were separated by filtration under reduced pressure, washed with a small amount of a saturated saline solution and then dried under reduced pressure.

The weight of the crystals obtained was 78.5 g, and the crystals were analyzed by HPLC to find that the content of 1-ethyl-5-hydroxypyrazole which was the desired compound was 94.4% by weight.

As impurity, 6.1% of sodium chloride was contained, but neither the isomer nor the 4,4'-adduct was contained. The crystal fraction and the filtrate fraction were analyzed to find that the weight ratio of sodium chloride to the desired compound was 0.4.

Method for analyzing sodium chloride:
potentiometric titration using 0.02N silver nitrate Comparative Example 1

While stirring 62.56 g (200 mmole) of a 19.2% ethylhydrazine aqueous solution, 15.48 g (133 mmole) of methyl 3-methoxypropionate was added dropwise to the solution at 40° C. over about 1 hour, and the mixture was reacted at 40° C. for 2 hours.

The pH of the solution before methyl 3-methoxypropionate was added dropwise thereto was 11.4. During the dropwise addition and after the dropwise addition, by adding a 48% sodium hydroxide aqueous solution dropwise to the mixture at a suitable time, the pH of the mixture was maintained at 10.0.

After completion of the reaction, the reaction mixture was analyzed by high performance liquid chromatography (HPLC) to find that methyl 3-methoxypropionate disappeared and 13.56 g (111 mmole) of 1-ethyl-5-hydroxypyrazole which was the desired compound was produced (yield: 83.6%)

An isomer and a 4,4'-adduct which were impurities were analyzed by HPLC to find that they were produced in amounts of 15.6 area % and 3.7 area % based on the amount of the desired compound, respectively.

Comparative Example 2

While stirring 50.05 g (160 mmole) of a 19.2% ethylhydrazine aqueous solution, 15.48 g (133 mmole) of methyl 3-methoxypropionate was added dropwise to the solution at 40° C. over about 1 hour, and the mixture was reacted at 40° C. for 2 hours.

The pH of the solution before methyl 3-methoxypropionate was added dropwise thereto was 11.4. At a point of time when the pH of the mixture became 9.5 after the dropwise addition, by adding a 48% sodium hydroxide aqueous solution dropwise to the mixture at a suitable time, the pH of the resulting mixture was maintained in the range of 9.4 to 9.6.

After completion of the reaction, the reaction mixture was analyzed by high performance liquid chromatography (HPLC) to find that methyl 3-methoxypropionate disappeared and 11.02 g (98 mmole) of 1-ethyl-5-hydroxypyrazole which was the desired compound was produced (yield: 73.7%).

An isomer and a 4,4'-adduct which were impurities were analyzed by HPLC to find that they were produced in amounts of 7.1 area % and 12.4 area % based on the amount of the desired compound, respectively.

Comparative Example 3

While stirring 31.28 g (100 mmole) of a 19.2% ethylhydrazine aqueous solution, 7.74 g (64 mmole) of methyl 3-methoxypropionate was added dropwise to the solution at 40° C. over about 1 hour, and the mixture was reacted at 40° C. for 4 hours.

The pH of the solution before methyl 3-methoxypropionate was added dropwise thereto was 11.4, and the pH after completion of the reaction was 7.9.

After completion of the reaction, the reaction mixture was analyzed by high performance liquid chromatography (HPLC) to find that methyl 3-methoxypropionate disappeared and 5.94 g (53 mmole) of 1-ethyl-5-hydroxypyrazole which was the desired compound was produced (yield: 82.9%).

An isomer and a 4,4'-adduct which were impurities were analyzed by HPLC to find that they were produced in amounts of 2.0 area % and 13.2 area % based on the amount of the desired compound, respectively.

Comparative Example 4

While stirring 31.28 g (100 mmole) of a 19.2% ethylhydrazine aqueous solution, a 48% sodium hydroxide aqueous solution was slowly added dropwise to the ethylhydrazine aqueous solution at 40° C. to adjust pH to 13.7.

Further, 7.74 g (64 mmole) of methyl 3-methoxypropionate was added dropwise to the mixture at 40° C. over about 1 hour.

After completion of the reaction, the reaction mixture was analyzed by high performance liquid chromatography (HPLC) to find that methyl 3-methoxypropionate disappeared and 2.15 g (19 mmole) of 1-ethyl-5-hydroxypyrazole which was the desired compound was produced (yield: 30.0%).

An isomer and a 4,4'-adduct which were impurities were analyzed by HPLC to find that they were produced in amounts of 258 area % and 4.5 area % based on the amount of the desired compound, respectively. The isomer was a main reaction product.

Comparative Example 5

In 30 ml of methanol was dissolved 11.6 g (100 mmole) of methyl 3-methoxypropionate, and 6.6 g (100 mmole) of 91.6% ethylhydrazine was slowly added dropwise to the solution.

The solution which was further reacted at room temperature for 24 hours was analyzed by HPLC to find that 7.5 g (67 mmole) of 1-ethyl-5-hydroxypyrazole which was the desired compound was produced (yield: 67%)

An isomer and a 4,4'-adduct which were impurities were produced in amounts of 0.4 area % and 10.8 area % based on the amount of the desired compound, respectively.

According to the present invention, 1-ethyl-5-hydroxypyrazole which is useful as an intermediate of an effective compound of a herbicide can be prepared with a good yield while generation of impurities is suppressed.

We claim:

1. A process of preparing 1-ethyl-5-hydroxypyrazole, which comprises reacting an alkyl 3-alkoxyacrylate represented by the following formula (1):

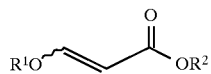

wherein R¹ and R² are the same or different from each other and each represents lower alkyl group, and ∾ in the formula represents either cis- or trans-configuration, with ethylhydrazine in an amount of 1- to 10-fold mole based on 1 mole of the alkyl 3-alkoxyacrylate in a weakly basic aqueous solvent, wherein the pH of the reaction mixture during the reaction is maintained at about 7.5 to about 10.

2. A process according to claim 1, wherein the process is performed by adding dropwise the alkyl 3-alkoxyacrylate to an ethylhydrazine aqueous solution.

3. A process according to claim 2, wherein a pH of an ethylhydrazine aqueous solution before the reaction is about 9.0 to about 10.0.

4. A process according to claim 2, wherein a pH of an ethylhydrazine aqueous solution before the reaction is about 9.2 to about 9.8.

5. A process according to claim 2, wherein a pH of a reaction mixture during dropwise addition is about 9.0 to about 10.0.

6. A process according to claim 2, wherein a pH of a reaction mixture during dropwise addition is about 9.2 to about 9.8.

7. A process according to claim 1, wherein the alkyl 3-alkoxyacrylate is methyl 3-methoxypropionate.

8. A process according to claim 1, wherein the amount of ethylhydrazine is 1- to 6-fold mole based on 1 mole of the alkyl 3-alkoxyacrylate.

9. A process according to claim 1, wherein the amount of ethylhydrazine is 1.5- to 5-fold mole based on 1 mole of the alkyl 3-alkoxyacrylate.

10. A process for isolating 1-ethyl-5-hydroxypyrazole, which comprises concentrating the reaction mixture obtained in claim 1 under reduced pressure to remove ethylhydrazine and then crystallizing the residue by salting out.

* * * * *